US008856298B2

(12) United States Patent
Blanch Torra et al.

(10) Patent No.: US 8,856,298 B2
(45) Date of Patent: Oct. 7, 2014

(54) METHOD AND SYSTEM FOR MANAGING RELATED-PATIENT PARAMETERS PROVIDED BY A MONITORING DEVICE

(75) Inventors: Lluis Blanch Torra, Barcelona (ES); Enric Laporte Rosello, Barcelona (ES); Bernat Sales López, Barcelona (ES); Gastón E. Murias, Barcelona (ES)

(73) Assignee: Corporacia Sanitaria Parc Tauli, Barcelona (ES)

( * ) Notice: Subject to any disclaimer, the term of this patent is extended or adjusted under 35 U.S.C. 154(b) by 197 days.

(21) Appl. No.: 12/528,940

(22) PCT Filed: Feb. 28, 2008

(86) PCT No.: PCT/EP2008/052458
§ 371 (c)(1),
(2), (4) Date: Sep. 22, 2009

(87) PCT Pub. No.: WO2008/104602
PCT Pub. Date: Sep. 4, 2008

(65) Prior Publication Data
US 2010/0106825 A1    Apr. 29, 2010

Related U.S. Application Data

(60) Provisional application No. 60/892,100, filed on Feb. 28, 2007.

(30) Foreign Application Priority Data

Feb. 28, 2007   (EP) ..................................... 07103251

(51) Int. Cl.
*G06F 15/173*   (2006.01)
*G06Q 10/00*    (2012.01)
*G06Q 50/00*    (2012.01)
*G06F 19/00*    (2011.01)

(52) U.S. Cl.
CPC ................................ *G06F 19/3418* (2013.01); *G06F 19/3443* (2013.01)
USPC .................... 709/223; 709/224; 705/1; 705/3

(58) Field of Classification Search
USPC ............ 709/217, 223–224; 705/1–3; 600/301
See application file for complete search history.

(56) References Cited

U.S. PATENT DOCUMENTS

| 3,815,109 A | 6/1974 | Carraway et al. |
| 4,784,162 A | 11/1988 | Ricks et al. |

(Continued)

FOREIGN PATENT DOCUMENTS

| WO | WO0241232 A2 | 5/2002 |
| WO | WO0241232 A3 | 5/2002 |

(Continued)

OTHER PUBLICATIONS

Quiroga, Event Synchronization: a simple and fast way to measure event synchronicity and time delay patterns, 2002.*

(Continued)

*Primary Examiner* — Shirley Zhang
(74) *Attorney, Agent, or Firm* — Roberts Mlotkowski Safran & Cole P.C.

(57) ABSTRACT

System (15) for managing related-patient parameters provided by at least one monitoring device (11 a, 11 b), the system comprising means for connecting said system to the monitoring device (11 a; 11 b); means for capturing, through the connection with the monitoring device, at least one patient-related parameter selected from a set of patient-related parameters provided by the monitoring device (11 a; 11 b); means for adapting the captured patient-related parameter to a predetermined parameter format; and means for managing the adapted patient-related parameter. The provision of adapting means allows managing data provided by any type of monitoring device.

23 Claims, 5 Drawing Sheets

(56) References Cited

U.S. PATENT DOCUMENTS

| | | | |
|---|---|---|---|
| 6,322,502 | B1 | 11/2001 | Schoenberg et al. |
| 7,039,878 | B2 * | 5/2006 | Auer et al. ............... 715/810 |
| 7,224,281 | B2 | 5/2007 | Santoso et al. |
| 2002/0087503 | A1 * | 7/2002 | Judd et al. ............... 707/1 |
| 2003/0036687 | A1 | 2/2003 | Schoenberg et al. |
| 2003/0158746 | A1 * | 8/2003 | Forrester ............... 705/1 |
| 2003/0182164 | A1 | 9/2003 | Shabot et al. |
| 2003/0200116 | A1 | 10/2003 | Forrester |
| 2004/0102693 | A1 * | 5/2004 | Jenkins ............... 600/410 |
| 2005/0125256 | A1 | 6/2005 | Schoenberg et al. |
| 2006/0161459 | A9 | 7/2006 | Rosenfeld et al. |
| 2008/0004904 | A1 * | 1/2008 | Tran ............... 705/2 |
| 2009/0055735 | A1 * | 2/2009 | Zaleski et al. ............... 715/700 |

FOREIGN PATENT DOCUMENTS

| | | |
|---|---|---|
| WO | WO2006003636 A1 | 1/2006 |
| WO | WO2008104602 A3 | 9/2008 |

OTHER PUBLICATIONS

J. M. Soto Ibáñez, N. Perales Rodríguez De Viguri y M. Ruano Marco para la Sociedad Española de Medicina Intensiva, Critica y Unidades Coronarias, Anexo I: Equipamiento De Urgencias, http://www.rcp.semicyuc.org/docs.htm. Statement of Relevance, 37 CFR 1.98: see p. 2, lines 6-21 of specification.

David F. Franklin and David V. Ostler, "Proposed Standard IEEE P1073 Medical Information Bus Medical Device to Host Computer Interface Network Overview and Architecture", Computers and Communications, 1989. Conference Proceedings. , Eight Annual International Phoenix Conference, p. 574-578, Mar. 22-24, 1989.

David F. Franklin and David V. Ostler, "The P1073 Medical Information Bus", Micro IEEE, Oct. 1989, p. 52-60.

Miguel Galarraga, Ignacio Martinez, Paula de Toledo, "Review of the ISO/IEEE 11073—PoCMDC standard for medical device interoperability and its applicability in home and ambulatory telemonitoring scenarios", 2006, p. 1-65.

Rosenfeld, B. A., T. Dorman, M. J. Breslow, P. Pronovost, M. Jenckes, N. Zhang, G. Anderson, and H. Rubin, "Intensive care unit telemedicine: alternate paradigm for providing continuous intensivist care", 2000, Crit Care Med vol. 28, No. 12, p. 3925-31.

Breslow, M. J., B. A. Rosenfeld, M. Doerfler, G. Burke, G. Yates, D. J. Stone, P. Tomaszewicz, R. Hochman, and D. W. Plocher, "Effect of a multiple-site intensive care unit telemedicine program on clinical and economic outcomes: an alternative paradigm for intensivist staffing", 2004, Crit Care Med vol. 32, No. 1, p. 31-8.

Dvir, D., J. Cohen, and P. Singer, "Computerized energy balance and complications in critically ill patients: an observational study", 2006, Clinical Nutrition, vol. 25, p. 37-44]).

* cited by examiner

METHOD AND SYSTEM FOR MANAGING RELATED-PATIENT PARAMETERS PROVIDED BY A MONITORING DEVICE

CROSS-REFERENCE TO RELATED APPLICATIONS

The present Application is a national phase of PCT/EP2008/052458 filed on Feb. 28, 2008 ("PCT Application"), which claims priority from European Application No. EP 07103251.0 filed on Feb. 28, 2007, and from U.S. Application 60/892,100, filed on Feb. 28, 2007, all three of which are hereby incorporated by reference in their entirety into the present Application, including any amendments made in the PCT application during the international phase.

The present invention relates to a method for managing, in a computer system, related-patient parameters provided by at least one monitoring device. More specifically, the invention relates to a method for obtaining, synchronizing, processing, storing and distributing biomedical and digital signals used in medical fields.

The invention also relates to a system for managing related-patient parameters provided by at least one monitoring device, suitable for carrying out such a method.

The invention is within the framework of the information technologies applied to the medicine.

BACKGROUND ART

Nowadays, it is true that in the TIC field related to health care, for example, in the management and transfer of data between hospital information systems, there is a defined standard (named HL7) which has a wide consensus (or the digital radiology case (DICOM)), but in the specific field of health monitoring devices the situation is different.

Although standards for the transmission of biomedical signals are known, they have not been used in a uniform way in the development of monitoring devices. This way, the industry offers monitoring devices whose communication protocol is defined, without any restriction, by the manufacturer.

This tendency and the diversity within the devices are shown not only in the data transmission protocols but also in their operation. The need to unify the transmission and operability criteria has not aroused yet because the signal capturing technology has not been sufficiently developed and consequently it has not been required for the existence of homogeneous devices.

These days, the software developing companies—less related to the sanitary field—and patient assistance device manufacturers follow two developing and marketing lines.

Firstly, the big companies tend to develop integrated suites, in which all the devices that compose them are company property, and the software solutions that they offer are only able to operate on the company devices. The fact that there is no references to devices from a specific manufacturer, for example, in the *"Sociedad Española de Medicina"* recommendations (*[J. M. Soto Ibáñez, N. Perales Rodríguez de Viguri y M. Ruano Marco para la Sociedad Española de Medicina Intensiva, Critica y Unidades Coronarias. ANEXO I: EQUIPAMIENTO DE URGENCIAS*. http://www.rcp.semicyuc.org/docs.html]), is partially responsible of that there are different devices from different manufacturers in the intensive medical services and in the coronary units (part of them operating for more than 30 years), said devices being excellent for its operation but incapable to communicate with other devices. This way, if a medical centre would like to implement a technological solution which would allow a local and remote monitoring, it would require a great investment together with a great technological transformation linked to the solution provided by the provider of medical technology.

On the other hand, the software developing companies tend to develop solutions to the patient management and the signal monitoring, although with limitations. Regarding to the monitoring, these systems work with tendencies, that is, an abstract of the vital signals of the patients. In some situations, these solutions are sufficient, although in other situations there is a need of information which said systems are not able to acquire or process. Beside said limitations, the great problem of these systems is the complexity of use of its interface, because of the great number of functions it offers.

There are a lot of systems offering a solution for the computerization of ICUs and patient monitoring scenarios, but said set of functions has been partially developed by two commercial implementations:

eICU Solution (VISICU®). The oldest. It was created as an implementation of telemedicine and it has added some functionalities. Its main limitation is that it interacts with the acquiring systems property of the monitor manufacturers and is limited to transmit them through a network. It does not transmit information from the mechanical ventilators. The usage of the system is wide and its implementation has shown a mortality, stay in the ICU and cost reduction ([Rosenfeld, B. A., T. Dorman, M. J. Breslow, P. Pronovost, M. Jenckes, N. Zhang, G. Anderson, and H. Rubin. 2000. *Intensive care unit telemedicine: alternate paradigm for providing continuous intensivist care. Crit. Care Med* 28:3925-31]; [Breslow, M. J., B. A. Rosenfeld, M. Doerfler, G. Burke, G. Yates, D. J. Stone, P. Tomaszewicz, R. Hochman, and D. W. Plocher. 2004. *Effect of a multiple-site intensive care unit telemedicine program on clinical and economic outcomes: an alternative paradigm for intensivist staffing. Crit. Care Med* 32:31-8]).

IMDSoft®. Newer, it has been initiated as a clinical information system and includes some functions of data transmission. The published reports have only evaluated the original application ([Dvir, D., J. Cohen, and P. Singer. 2006. *Computerized energy balance and complications in critically ill patients: an observational study. Clin Nutr* 25:37-44]).

In summary, the known systems are dependents of the type and/or manufacturer of the monitoring devices (for example, each monitoring device has a communication protocol defined by its manufacturer and, consequently, it cannot establish a connection with a device or system of another manufacturer, because they do not "understand"). Consequently, a change in a system of a monitoring device (for example, because the device has broken) involves a great investment together with a great technological transformation.

DISCLOSURE OF THE INVENTION

It is therefore an object of the invention to provide a system for managing patient-related parameters provided by at least one monitoring device, said monitoring device being any monitoring device, independently of its type or manufacturer, together with digital signals, such as audio and video.

This object is achieved in accordance with claim 1 by providing a system for managing related-patient parameters provided by at least one monitoring device, the system comprising means for connecting said system to the monitoring device; means for capturing, through the connection with the monitoring device, at least one patient-related parameter selected from a set of patient-related parameters provided by the monitoring device; means for adapting the captured patient-related parameter to a predetermined parameter format; and means for managing the adapted patient-related parameter.

This way, the provision of the means for adapting the captured patient-related parameter to a predetermined parameter format allows managing patient-related parameters provided by any type (or manufacturer) of monitoring device, that is, the system may capture data from any type of monitoring device and manage it. For example, it may be a new monitoring device with its associated protocol defined by the manufacturer or it is also possible to implant the system in hospitals with a diversity of monitoring devices, without changing said devices. Basically, it is obtained a homogeneous system in front of the heterogeneous supply of monitoring devices.

It is important to highlight that the system can capture data provided by any type of the monitoring device because the communication protocols of the computer system and the monitoring device are adapted according to its specifications.

Basically, the system captures and synchronise the values. Subsequently, for each defined period, the system interpolates the captured values according to the defined virtual frequency (N points per second). Previously, the virtual frequency and the period have been defined.

Each monitoring device comprises a communication protocol defined by its manufacturer and, consequently, it is different from one to another device. For this reason, the system must offer (besides of implementing the needed communication protocols) a format and common interface to the signals obtained from the devices, each one having its specific implementation of it, according to its communication protocol. That is, the system according to the invention is not compatible with a monitoring device until the corresponding protocol is implemented and integrated in the system.

A monitoring device may be any device providing biomedical signals (for example, a monitor, a respiration device or any device for providing patient-related parameters) and/or video/audio signals (i.e. digital signals) used in medical fields.

Another advantage of the invention is that, with the digital and biomedical signal centralization, the system allows having at one's disposal of a homogeneous interface, highly customizable according to the preferences of the users, independently of the origin of the signals that are being captured, displayed, processed and stored.

In a preferred embodiment of the invention, the system comprises means for detecting and processing predetermined clinical events, that is, an expert system. Said expert system gives support in real time for detecting clinical events that are considered relevant for the health professionals. Consequently, the expert system improves the medical assistance to the patients because it provides tools for developing a better diagnosis and treatment (the possibility of errors is reduced).

In a preferred embodiment of the invention, the system comprises a first repository for storing the patient-related parameters. Further, it is possible to store in said first repository (e.g. a database of patient-related parameters) the time when the patient-related parameters are captured. The system, from said stored times, may perform the synchronisation of the parameters. Basically, the system stores the parameters and the time when they are captured.

Subsequently, the system interpolates (for each period previously defined) synchronising according to the captured times and the delay of the device. The system reads the values at each defined period.

On the other hand, the system may comprise a second repository for storing the clinical history of the patients. Further, it is also possible to store (in the same or another repository) the data with the hospital information systems.

Consequently, it is possible to combine the information of all repositories and obtain a tool that improves the access and availability of the information relating to the patients. An integration of all patient data is achieved.

In any case, the stored data in the repositories may be a source of information for the expert system described above. Said information allows adjusting the variables and values of the expert system which update its knowledge base (rules for processing data) from said information.

The patient-related parameter may be selected from the following set of parameters: EKG, PLET, PAW, airflow, TA and expired PCO2. EKG relates to an electrocardiogram and it is suitable for detecting fast and slow arrhythmias; PLET relates to a pulse oximetry, which detects oxygen saturation in the haemoglobin; PAW relates to the pressure depending on the time elapsed when the air enters from an artificial respirator to the lungs; Airflow relates to the liters per second of air infused from the artificial respirator to the lungs; TA relates to the arterial pressure; and expired CO2 relates to the CO2 in blood.

According to another aspect of the invention, it is provided a method for managing, in a computer system, patient-related parameters provided by at least one monitoring device, the method comprising the steps of (A) connecting the computer system to the monitoring device; (B) capturing, through the connection with the monitoring device, at least one patient-related parameter selected from a set of patient-related parameters provided by the monitoring device; (C) adapting the captured patient-related parameter to a predetermined parameter format; and (D) managing the adapted patient-related parameter.

According to a preferred embodiment of the invention, steps (B) to (D) of the method are repeated after predetermined periods of time. Said periods of time are defined by the system according to the invention and not by the monitoring device. The monitoring device provides data but the system captures said data according to its definition of periods of time.

The method further comprises a step (E) of obtaining, from a user input, the monitoring device to be connected. Since the computer system has connected several monitoring devices, it is needed to select the devices from which the user system wants to obtain data.

Preferably, the method comprises a step (F) of determining the parameter format.

The method may also comprise a step (G) of adapting the communication protocols of the computer system and the monitoring device for establishing a connection between them.

According to an embodiment of the invention, step (D) of managing the adapted patient-related parameter comprises a sub-step (D.1) of storing said adapted patient-related parameter in a first repository.

In said sub-step (D.1), the adapted patient-related parameter stored in the first repository may comprise the parameter and the time when the parameter is captured. Further, the adapted patient-related parameter also may comprises audio and video signals obtained at the time of capturing the parameter. On the other hand, said repository may be a temporal repository.

According to another embodiment of the invention, in sub-step (D.1), the adapted patient-related parameter is stored in DICOM objects. DICOM is a standard for transmitting and storing multimedia data in the medical field (for example, radiological pictures) including physiological signals obtained from the patient monitoring devices. The standardization of DICOM involves great advantages, for example, the easy integration with the hospital information systems. In this way, the captured signals are accessible from any system that implements DICOM.

According to an embodiment of the invention, step (D) of managing the adapted patient-related parameter comprises a sub-step (D.2) of displaying said adapted patient-related parameter.

According to another embodiment of the invention, step (D) of managing the adapted patient-related parameter comprises a sub-step (D.3) of distributing said adapted patient-related parameter to at least another computer system.

In another embodiment of the invention, the patient-related parameter comprises physiological signals and/or audio/video signals. In this case, the system synchronises all data related with the patient-related parameters, that is, the system synchronises the parameters, the physiological signals and the video and audio signals.

According to another aspect, the invention provides a computer program comprising program instructions for causing a computer to perform the method for managing patient-related parameters coming from at least one monitoring device. Said computer program may be embodied on storing means (for example, on a record medium, on a computer memory or on a read-only memory) or carried on a carrier signal (for example, on an electrical or optical carrier signal).

BRIEF DESCRIPTION OF THE DRAWINGS

In the following detailed description of some possible embodiments, other features and advantages of the invention will appear, each description being made with reference to the following drawings.

DETAILED DESCRIPTION

Following, a description of a preferred embodiment of the invention will be described according to the drawings. In this description, the system for managing related-patient parameters provided by at least one monitoring device is presented in the form of a computer program running on a computer.

The concept of the homogeneous system is based in the definition of a virtual parameter, that is, the patient-related parameter adapted according to the predetermined parameter format. Consequently, a virtual parameter is the representation in the system of the captured parameters and univocally represents a same parameter, independently of its origin device. Each virtual parameter is associated with a virtual device, which features and definition allow to the system offering a generic interface representing, in a homogeneous manner, the data captured in any scenario of capture.

The virtualization of the parameters is the translation of the parameters of a device to predetermined parameters of the system:

For example:
Device 1: it comprises the following parameters:
D1-ECG
D1-TA
D1-PLET
Device 2: it comprises the following parameters:
D2-ECG
Device 3: it comprises the following parameters:
D3-ECG
D3-PLET The virtual parameters of the system are: ECG, TA and PLET.

Consequently, according to an example of virtualization:

| Device | Parameter of device | Virtual parameter |
|---|---|---|
| Device 1 | D1-ECG | ECG |
|  | D1-TA | TA |
|  | D1-PLET | PLET |
| Device 2 | D2-ECG | ECG |
| Device 3 | D3-ECG | ECG |
|  | D3-PLET | PLET |

Thus, the system can process a parameter in the same way, for example, the ECG parameter, independently of capturing the parameter from the device 1, 2 or 3. The system works with the original parameter after the virtualization of the parameter. This way, the parameters are displayed and stored in the same way since said information is associated with the virtual parameters rather than real parameters.

This way, for example, it is possible to define a profile of capture in which:

Parameters to capture (i.e. virtual parameters): ECG and PLET;

Devices from which the parameters are captured: Device 1.

Then, the systems connects to the Device 1, searches if the Device 1 comprises real parameters corresponding to the selected virtual parameters (ECG and PLET), and automatically configures D1-ECG and D1-PLET for obtaining values.

If the devices from which the parameters are captured are Device 1 and Device 2 (more than one device), the system finds the two devices (or more) because the two devices comprise the parameters ECG and PLET. Then, the system should ask the user which device must be used.

On the other hand, the patient-related parameters comprises EKG (it relates to an electrocardiogram and it is suitable for detecting fast and slow arrhythmias); PLET (it relates to a pulse oximetry, which detects oxygen saturation in the haemoglobin); PAW (it relates to the pressure depending on the time elapsed when the air enters from an artificial respirator to the lungs); Airflow (it relates to the liters per second of air infused from the artificial respirator to the lungs); TA (it relates to the arterial pressure; and expired CO2 relates to the CO2 in blood).

After an accurate study, professionals have determined that from the vast amount of information that patient monitoring devices may provide, the information derived from as few as six vital signs (cited above) is sufficient to guarantee satisfactory control of critical patients. This approach ensures that the most important information is available and that the professional will not be overwhelmed with data.

Figure 1:
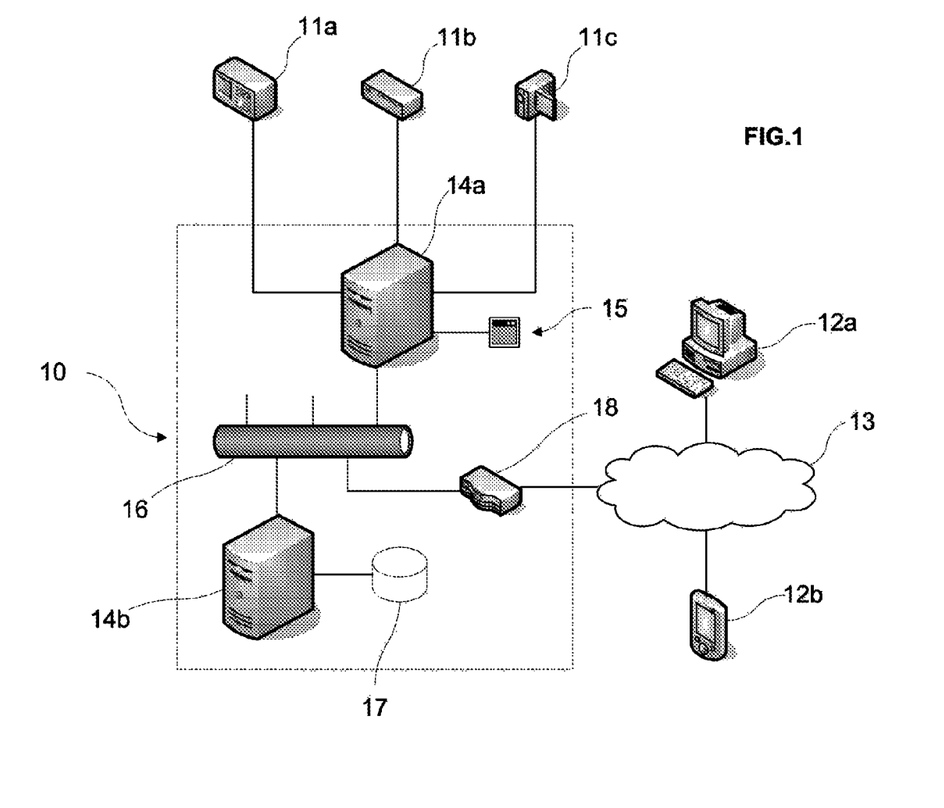
FIG. 1 is a schematic diagram illustrating a medical facility comprising the system for managing patient-related parameters provided by at least one monitoring device, according to the invention.

FIG. 1 shows an example of a medical facility for monitoring patients. More specifically, FIG. 1 shows an ICU facility. Said facility comprises a computer system 10 for capturing, processing, storing, synchronising, interpolating and distributing physiological signals (or biomedical signals) and video/audio signals; a first monitoring device, represented by a monitor 11a, for providing patient physiological signals (i.e. patient-related parameters) to the computer system 10; a second monitoring device, represented by a mechanical ventilation apparatus 11b, for also providing physiological signals (i.e. patient-related parameters) to the computer system 10; and a device, represented by a digital camera 11c, for providing audio/video signals (i.e. patient-related parameters) to the computer system 10.

Further, the facility also comprises a personal computer 12a and a Personal Digital Assistant (PDA) 12b remotely arranged from the computer system's 10 point of view, said personal computer 12a and said PDA 12b being connected to the computer system 10 through a global communication network 13, such as Internet. Said personal computer 12a and PDA 12b are suitable for monitoring remotely the patient because the computer system 10 distributes the patient-related parameters to them. Obviously, the system, for distributing the parameters, comprises a security system that secures said distribution.

The computer system 10 comprises a first computer 14a (e.g. a server) to which the monitor 11a, the mechanical ventilation apparatus 11b and the digital camera 11c are connected; a computer program 15, running on said first computer 14a, which represents the system, according to the invention, for managing patient-related parameters provided by the monitor 11a, the ventilation apparatus 11b and the digital camera 11c; a second computer 14b (e.g. a data server) connected to the first computer 14a through an Ethernet network 16 (for example, by means of a switch); a database 17, stored in a hard disk (not shown) connected to said second computer 14b, for storing the captured and adapted patient-related parameters (including the audio/video signals), the clinical history of the patients and the data of the hospital information systems (that is, all information about the patients is integrated in the database); and a router 18 for connecting the computer system 10 (more specifically, the Ethernet network 16) to the global communication network 13, the router 18 being connected to the switch, for providing a communication between the first and second computers 14a,14b and the personal computer 12a and the PDA 12b. This way, the computer system 10, by means of the first computer 14a and through the global communication network 13, distributes the captured and adapted patient-related parameters to the personal computer 12a and the PDA 12b (that is, it is possible to perform a remote monitorization of a patient), and said personal computer 12a and said PDA 12b may query information in the database 17.

The first computer 14a comprises a network interface for connecting to the Ethernet network 16 and an input/output interface for each monitoring device 11a,11b and the camera 11c to be connected. The second computer 14b comprises a network interface for connecting to the Ethernet network 16 and an input/output interface for connecting to the hard disk, in case of the hard disk was an external device, for example, an USB disk. The monitoring devices 11a,11b and the camera 11c comprise an input/output interface for connecting to the first computer 14a. The personal computer 12a comprises a network interface for connecting to Internet 13 whereas the PDA 12b also comprises a network interface (for example, a wireless interface) for connecting to Internet 13.

Obviously, the computer system 10 may show different configurations. Thus, for example, it may comprise only one computer or more than two computers or one computer locally arranged and another computer remotely arranged. In the last case, the two computers must be connected through a global communication network, for example, Internet.

On the other hand, the personal computer 12a or the PDA 12b may be locally arranged from the computer system's 10 point of view, that is, they are connected to the same LAN (Local Area Network). Thus, a local monitorization is performed, for example, from the same patient hospital room or from the health professional office.

Further, the connection between the monitoring devices and the first computer 14a may be performed trough a wireless network. In the same manner, the first and the second computer 14a,14b may be connected through a wireless network and said computers 14a,14b may connect to Internet 13 via a wireless connection with the router 18.

Figure 2:
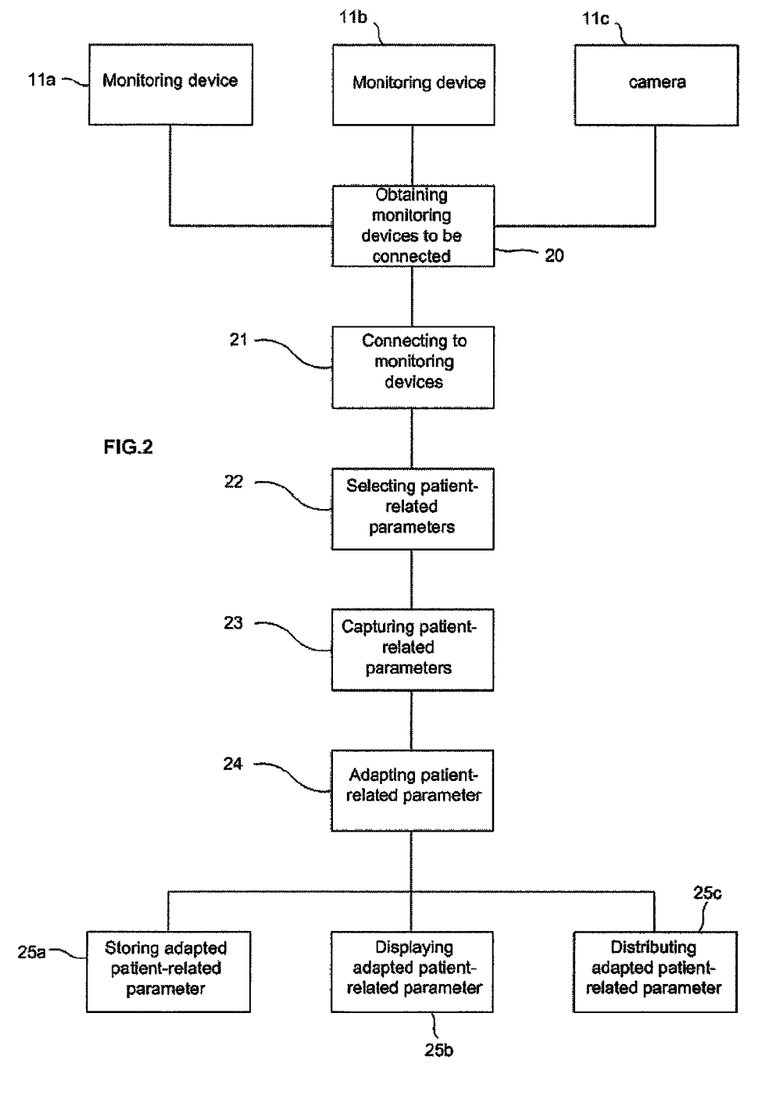
FIG. 2 is a schematic diagram illustrating the system for managing patient-related parameters provided by at least one monitoring device, according to the invention.

There is a defined class in the system 15 according to the invention that represents any device which data may be captured from, and similarly, a class which represents any parameter being monitored.

In one hand, the class (object) which represents any device is a superclass from which the implementations of the protocols, which are implemented in the system, are inherited. That is, the protocols' implementation of any device is a specialization of this "generic" device. Obviously, the generic device does not contain the implementation of any protocol, and it only defines the scheme for the implementation to follow, also offering a group of routines (integrated in the system) for the implementations of the different protocols to use for integrating and adapting the data.

The generic device defines, for example, a routine to connect and obtain the list of parameters, another one to disconnect and one to initialize the data capture, which the protocols' implementations inherit (given that they are a specialization of the generic device). These are methods without implementation, only defined, which the protocols should full. This way, the system knows that for any implementation of the "connect" routine it will do the connection and obtain the parameter list, without being necessary the system to know the implementation.

On the other side, the generic device, and therefore any of the protocols' implementations, has a list of parameters associated as defined by the system. These parameters are also visible by the protocols' implementations, which only define the features for each of them (name, period/frequency—number of points per second which the protocol uses to transmit it—, minimum value, maximum value, etc.), as defined in the correspondent communications protocol. The parameter class offers several previously implemented routines to be used by different devices, such as "Add points"—which adds the points received to the captured values list of the correspondent parameter—.

The parameter class offers a routine to obtain the captured values in a period of time. The system 15, by means of a temporizer, requests continuously the parameters from the devices whose values are being captured. The system defines the periods, and the moments when said values are requested, and above all, the desired resolution, that is, the number of points per second which it wants the parameter to return the correspondent values. The parameter class has implemented the algorithm for obtaining the values in any frequency, and also the inter-class synchronization (that is, all the parameters will be synchronized, and the returned values in a moment T will correspond to the moment T of any of the active parameters).

Basically, if the delay of the device for providing data is known, the time for capturing a value can be defined as follow:

ACTUAL_TIME−DEVICE_DELAY= PRODUCTION_TIME

For the wave-type signals, once a time a first value is stored, the following times of capture ponder the theoretical time:

PREVIOUS_TIME_PRODUCTION+PARAMETER PERIOD

And the real time:

ACTUAL_TIME−DEVICE_DELAY

The values are synchronized according the following description.

The synchronization of the parameters is performed according the following description.

For each device, it is necessary to define which is the delay for sending data. Said delay depends on the communication protocol of the device. Said delay can be negligible or can be a few seconds. Because said delay is not specified, it must be experimentally obtained.

For example, D1, D2, D3, . . . , DN relates to devices and R1, R2, R3, . . . , RN are the delays associated to said devices. If Di is any of said devices from which data is being captured, in a time Tj, the value Vj corresponds to the time Tj−Ri, since Ri is the defined delay associated to the device Di.

The obtained values are in real time. This way, all values are synchronized.

An Example of Synchronization
Devices:
 D0: delay of 0 seconds;
 D1: delay of 1 second;
 D2: delay of 2 seconds;
 D3: delay of 3 seconds (it is the slowest device, with a 3 seconds of delay).
In a time T=0, values from D0, D1, D2 and D3 are obtained:
Real time of the value obtained from D0: 0−0=0
Real time of the value obtained from D1: 0−1=−1
Real time of the value obtained from D2: 0−2=−2
Real time of the value obtained from D3: 0−3=−3
In a time T=1, values from D0, D1, D2 and D3 are obtained:
Real time of the value obtained from D0: 1−0=1
Real time of the value obtained from D1: 1−1=0
Real time of the value obtained from D2: 1−2=−1
Real time of the value obtained from D3: 1−3=−2
In a time T=2, values from D0, D1, D2 and D3 are obtained:
Real time of the value obtained from D0: 2−0=2
Real time of the value obtained from D1: 2−1=1
Real time of the value obtained from D2: 2−2=0
Real time of the value obtained from D3: 2−3=−1
In a time T=3, values from D0, D1, D2 and D3 are obtained:
Real time of the value obtained from D0: 3−0=3
Real time of the value obtained from D1: 3−1=2
Real time of the value obtained from D2: 3−2=1
Real time of the value obtained from D3: 3−3=0

Consequently, the time stored in the repository associated to the value is the real time (time-delay) and not the reading time.

Thus, for knowing the value read from each device in T=0 it is necessary to wait until the second 3 (before said second 3 it is not possible to know the value read from D3 in the second 0). For this reason, the representation of the real time and synchronized values uses a delay corresponding to the greater delay of the considered devices.

In summary, the parameter class is able to return the received values with an X frequency of a P parameter re-sampled with a Y frequency and synchronized with all of the other monitored parameters; Ideally, Y>=X, although the algorithm for the interpolation (re-sampling) may be the most precise as possible and the signal being as accurate as possible to the original signal, independently of X and Y.

As can be seen in FIG. 2, the computer program 15 representing the system, according to the invention, for managing patient-related parameters provided by the monitor 11a, the ventilation apparatus 11b and the digital camera 11c comprises a first module 20 for obtaining, from a user input, the monitoring devices to be connected to the computer system; a second module 21 for connecting the computer system 10 (that is, the first computer 14a) to the obtained monitoring devices 11a,11b and the camera 11c; a third module 22 for selecting the patient-related parameters to be captured from a monitoring device; a fourth module 23 for capturing patient-related parameters provided by a monitoring device; a fifth module 24 for adapting the captured patient-related parameters according to a predetermined parameter format; and a sixth module 25 for managing the adapted patient-related parameters.

The fifth module 24 for adapting the captured parameters comprises a sub-module for synchronizing the values of the captured parameters.

The module 25 for managing the adapted patient-related parameters comprises a first sub-module 25a for storing the adapted patient-related parameters in the database 17, through the Ethernet network 16; a second sub-module 25b for displaying the adapted patient-related parameters (previously synchronized) by means of a graphic user interface in a computer monitor or a television set, the computer monitor or the TV being locally arranged from the computer system's 10 point of view; and a third sub-module 25c for distributing the adapted patient-related parameters to the personal computer 12a and/or the PDA 12b.

It is important to highlight that said module 25 for managing the adapted patient-related parameters must not be modified if a monitoring device is changed or a new monitoring device is connected to the facility. The data managed for this module is adapted to the predetermined parameter format cited above. Consequently, the management of said adapted patient-related parameters is independent of the type (or manufacturer) of the monitoring devices.

The sub-module 25a for storing the adapted patient-related parameters stores the parameters and the time when the parameters are captured to be subsequently consulted. Said storing sub-module 25a also stores the captured audio/video signals. Said query may be performed from a locally arranged computer (through the Ethernet network 16) or from a remotely arranged computer (through the global communication network 13). Thus, said stored information may be accessed by an expert system for adjusting its variables and values, said expert system updating its knowledge base (data processing rules) from said information.

The information is stored in DICOM objects, which is a standard for transmitting and storing multimedia data in the medical field (for example, radiological pictures) including physiological signals obtained from the patient monitoring devices. The standardization of DICOM involves great advantages, for example, the easy integration with the hospital information systems. In this way, the captured signals are accessible from any system that implements DICOM.

The sub-module 25b for displaying the adapted patient-related parameters generates the user interfaces (for example, graphic user interfaces) needed for displaying said parameters (see FIG. 4 and FIG. 5) to the users. Said interfaces always display the patient-related parameters according to the predetermined parameter format and the video signal associated to the parameters. Obviously, all information displayed in the interface are previously synchronized because the synchronization is performed before generating the interface. Thus, in case of change of a monitoring device or connection of a new monitoring device, the interfaces must not be changed or modified. The interfaces are independent of the type of the monitoring devices.

The sub-module 25c for distributing the adapted patient-related parameters to the personal computer 12a and/or the PDA 12b allows the remote monitorization of a patient. Further, said sub-module of distribution also allows querying and obtaining the desired information from the database 17.

The computer program 15 also comprises a module for determining the parameter format to which the patient-related parameters must be adapted and a module for adapting the communication protocols of the computer system and the monitoring device for exchanging data between them.

Furthermore, the computer program comprises a module for detecting and processing predetermined clinical events and an expert system for generating alarms when a relevant event is detected. Basically, said expert system offers a real time support for detecting clinical events that the health professionals consider relevant, said relevant events being defined by a clinical expert group.

Figure 3:
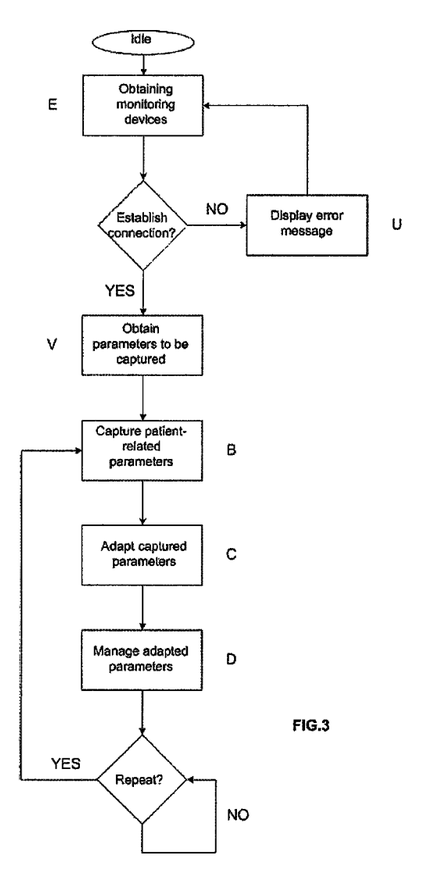
FIG. 3 is a flow chart illustrating the method for managing patient-related parameters provided by at least one monitoring device, according to the invention.

Following, a preferred embodiment of the method for managing patient-related parameters provided by at least one monitoring device (e.g. the monitor 11a, the mechanical ventilator 11b) and the digital camera 11c will be described.

Starting from an idle state, a user executes the computer program and it recovers from the first computer 14a the parameters of the implemented devices, said parameters corresponding with the virtual parameters (that is, the adapted parameters). In a step E, the first module 20 obtains the monitoring devices (e.g. the monitor 11a, the mechanical ventilator 11b) and the digital camera 11c to be connected with the first computer 14a (said monitoring devices must be configured, if it is required) and, in a step A, the second module 21 establishes a connection between the obtained monitoring devices 11a,11b and the camera 11c, and the computer system 10. In case of negative result for connecting the computer system 10 and all monitoring devices 11a,11b, and the camera 11c, in a step U, an error message is displayed and the control of the method goes to step E.

If the connection is established between the computer system 10 (more specifically, the first computer 14a) and all obtained devices 11a,11b,11c, that is, a positive result is obtained, in a step V, the third module 22 obtains the parameters to be captured from each monitoring device and, in a step B, the forth module 23 captures the patient-related parameters including the audio/video signals. Next, in a step C, the fifth module 24 adapts (synchronizes, etc.) the captured parameters according to the predetermined parameter format and, in a step D, the sixth module 25 manages the adapted parameters.

Said sixth module 25 comprises the first sub-module 25a which, in a sub-step D.2, generates a user interface (see FIG. 4 and FIG. 5) for displaying the adapted parameters. It is important to highlight that the displayed parameters always have the same format. Thus, if a new monitoring device is connected to the computer system 10, a change in the first sub-module 25a is not needed because the captured parameters are adapted to the predetermined parameter format. The interface always displays data in the same format independently of the monitoring device.

On the other hand, the second sub-module 25b, in a sub-step D.3, distributes the adapted parameters to other computers, for example, the personal computer 12a and the PDA 12b. In this manner, a remote monitorization may be performed.

Furthermore, the third sub-module 25c, in a sub-step D.1, stores the adapted parameters in the database 17. The stored parameter comprises the parameter, the time when the parameter was obtained and the audio/video signal associated to said parameter and time. Thus, the information is accessible, for example, for the expert system or from the personal computer 12a and the PDA 12b.

Obviously, it is possible to store, distribute and display each time an adapted parameter, that is, at least one of the sub-modules 25a,25b,25c must be executed.

It is important to highlight that the steps B to D may be repeated after predetermined periods of time. This way, the system according to the invention captures, adapts and manages data in a continually manner. Consequently, the system captures the values of the parameters every period of time (X seconds) previously defined.

Figure 4:
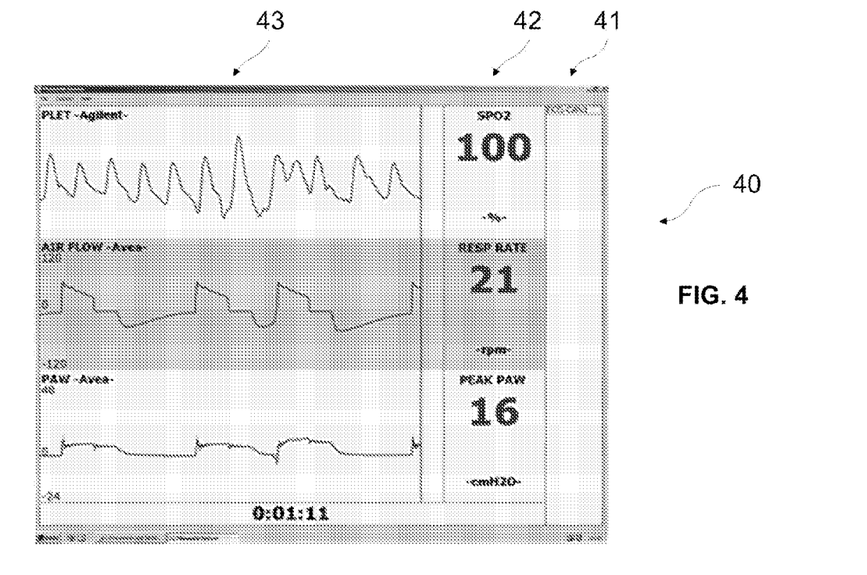
FIG. 4 is a schematic diagram illustrating a first graphical user interface generated by the system of FIG. 2.
Figure 5:
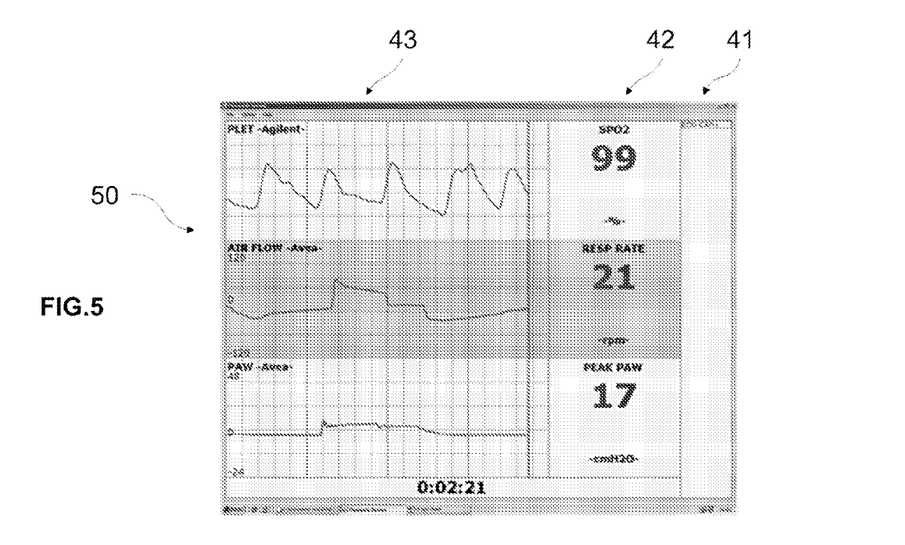
FIG. 5 is a schematic diagram illustrating a second graphical user interface generated by the system of FIG. 2.

FIG. 4 and FIG. 5 show two different graphic user interfaces for displaying the parameters adapted according to the predetermined parameter format.

Figure 6:
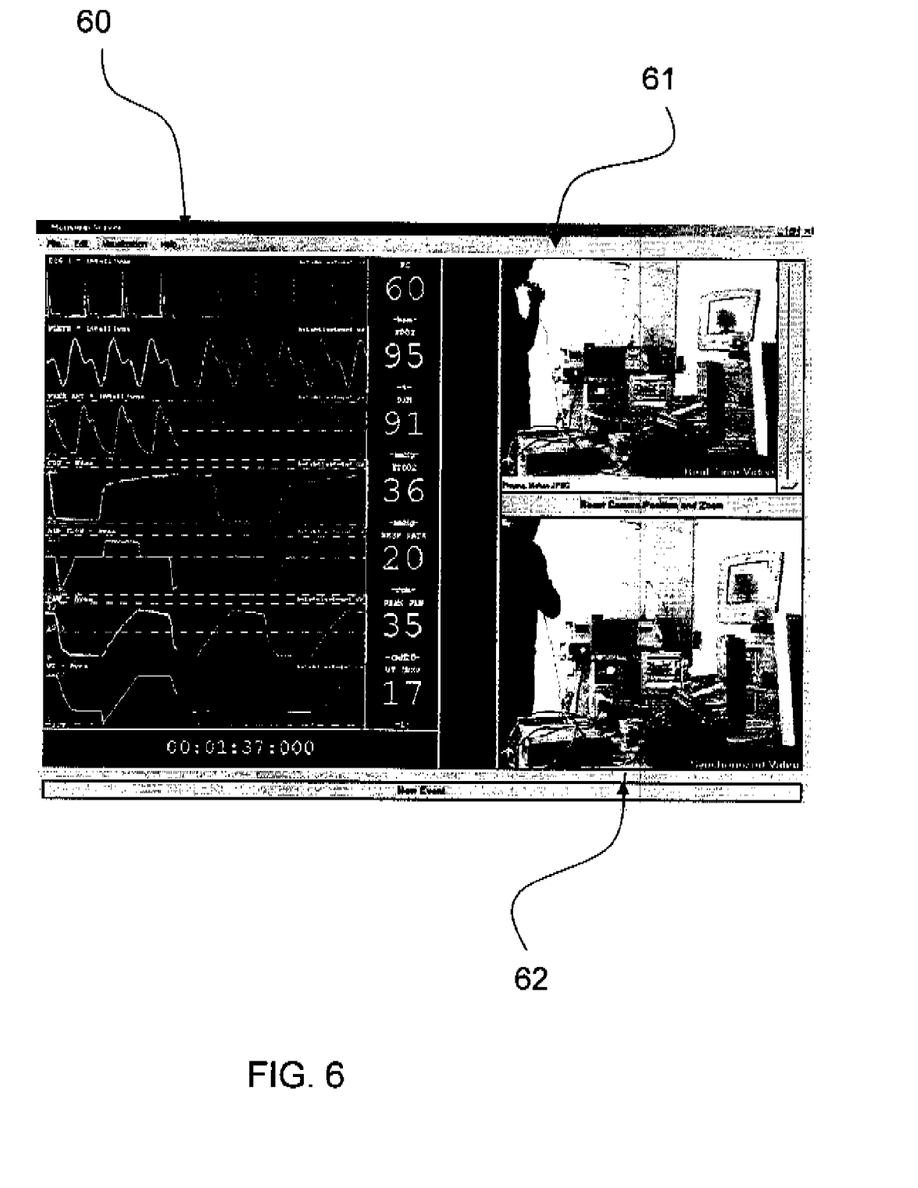
FIG. 6 is a schematic diagram illustrating a third graphical user interface generated by the system of FIG. 2.

FIG. 6 shows a further graphic user interface which comprises a signal display zone 60, which displays signals such as ECG or PLETH signals, and also comprises a first video display zone 62 which shows a video signal synchronized with the signal display, and a second video display zone 61 which shows a real-time video signal.

The fact of making the DICOM objects visually displayable increases the possibilities for interactive exchanges and helps professionals take full advantage of the information. Further, DICOM objects allow storing all information relating to the wave, so that it is possible a subsequent reconstruction. Furthermore, said information is integrated with the clinical history of the patient.

Although the present invention has been described in detail for purpose of illustration, it is understood that such detail is solely for that purpose, and variations can be made therein by those skilled in the art without departing from the scope of the invention.

Thus, while the preferred embodiments of the methods and of the systems have been described in reference to the environment in which they were developed, they are merely illustrative of the principles of the invention. Other embodiments and configurations may be devised without departing from the scope of the appended claims.

Further, although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source code, object code, a code intermediate source and object code such as in partially compiled form, or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When the program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A method for managing, in a computer system, patient-related parameters provided by at least one monitoring device, the method comprising the steps of:
   A) connecting the computer system to said at least one monitoring device;
   B) capturing, through the connection with the monitoring device, one or more physiological patient-related parameters selected from a set of patient-related parameters provided by said at least one monitoring device, wherein the capturing comprises:
      requesting continuously signal values for the one or more physiological patient-related parameters during a defined period of time;
      recording a time of capture for each signal value requested during the defined period of time;
      obtaining a delay of the at least one monitoring device in sending the signal values; and
      determining an actual time of capture for each signal value based at least on the time of capture for each signal value and the delay obtained for the at least one monitoring device;
   C) adapting each of the captured one or more physiological patient-related parameters to a predetermined parameter format to define a virtual parameter, said virtual parameter being a representation in the computer system of the captured one or more physiological patient-related parameters, which univocally represents a parameter independently of its device of origin; and
   D) managing the adapted one or more physiological patient-related parameters, wherein the managing comprises synchronizing each signal value captured for the one or more physiological patient-related parameters from said at least one monitoring device with signal values captured for one or more other physiological patient-related parameters captured from another monitoring device using the actual time of capture such that the synchronization takes account of the delay from the at least one monitoring device.

2. A method according to claim 1, wherein said one or more physiological patient-related parameters are provided by at least a first monitoring device and a second monitoring device.

3. A method according to claim 2, wherein the one or more physiological patient-related parameters captured from said first monitoring device and said second monitoring device are synchronized.

4. A method according to claim 3, wherein said captured one or more physiological patient-related parameters are synchronized taking into account a first delay for sending data of said first monitoring device and a second delay for sending data of said second monitoring device.

5. A method according to claim 4, wherein said first delay or said second delay is experimentally obtained.

6. A method according to claim 1, wherein steps (B) to (D) are repeated after predetermined periods of time.

7. A method according to claim 1, further comprising a step (E) of obtaining, from a user input, the monitoring device to be connected.

8. A method according to claim 1, further comprising a step of adapting the communication protocols of the computer system and the monitoring device for establishing a connection between them.

9. A method according to claim 1, wherein step (D) of managing the adapted one or more physiological patient-related parameters comprises a sub-step (D.1) of storing said adapted one or more physiological patient-related parameters in a first repository.

10. A method according to claim 9, wherein, in sub-step (D.1), the adapted one or more physiological patient-related parameters stored in the first repository comprises the adapted one or more physiological patient-related parameters and a time of capturing the adapted one or more physiological patient-related parameters.

11. A method according to claim 10, wherein the adapted one or more physiological patient-related parameters stored in the first repository further comprises video and audio signals obtained at the time of capturing the adapted one or more physiological patient-related parameters.

12. A method according to claim 9, wherein, in sub-step (D.1), the adapted one or more physiological patient-related parameters is stored as objects in accordance with Digital Imaging and Communications in Medicine (DICOM) standard.

13. A method according to claim 12, wherein step (D) of managing the adapted one or more physiological patient-related parameters comprises a sub-step (D.2) of displaying said adapted one or more physiological patient-related parameters.

14. A method according to claim 13, wherein step (D) of managing the adapted one or more physiological patient-related parameters comprises a sub-step (D.3) of distributing said adapted one or more physiological patient-related parameters to at least another computer system.

15. The method according to claim 1, wherein the one or more physiological patient-related parameters is selected from the group consisting of electrocardiogram signals, pulse oximetry signals, artificial respirator pressure signals, airflow signals, arterial pressure signals, and $CO_2$ signals.

16. The method according to claim 1, wherein the captured one or more physiological patient-related parameters comprise a sequence of data points measured from a patient at successive points in time spaced at uniform time intervals.

17. The method according to claim 1, wherein the one or more physiological patient-related parameters include values captured over a defined period of time.

18. A system for managing patient-related parameters comprising:
   a plurality of monitoring devices;
   a router;
   a communication network;
   an electronic device having a display; and
   a server connected to said plurality of monitoring devices and configured to:
      capture through the connection with the monitoring devices, at least one physiological patient-related parameter selected from a set of patient-related parameters provided by the monitoring devices, wherein the capture comprises:
         requesting continuously signal values for the at least one physiological patient-related parameter during a defined period of time;

recording a time of capture for each signal value requested during the defined period of time;

obtaining a delay of the monitoring devices in sending the signal values; and determining an actual time of capture for each signal value based at least on the time of capture for each signal value and the delay obtained for the monitoring devices; and adapt the captured at least one physiological patient-related parameter to a predetermined parameter format to define a virtual parameter, said virtual parameter being a representation in the system of the captured at least one physiological patient-related parameter, which univocally represents a parameter independently of its device of origin, and manage the adapted at least one physiological patient-related parameter by synchronizing each signal value captured for the at least one physiological patient-related parameter from said monitoring devices with signal values captured for at least one other physiological patient-related parameters captured from another monitoring device using the actual time of capture such that the synchronization takes account of the delay from the monitoring devices wherein said server is connected to the communication network through the router, and the electronic device having said display is connected to the communication network, such that real-time remote monitoring of a patient is possible.

19. A system according to claim 18, wherein the server is further programmed to detect and process predetermined clinical events.

20. A system according to claim 18, further comprising a first repository for storing the captured at least one physiological patient-related parameter.

21. A system according to claim 18, further comprising a second repository for storing a clinical history of the patients.

22. A system according to claim 18, wherein the captured at least one physiological patient-related parameter is provided by at least one monitoring device selected from the group consisting of: electrocardiogram (EKG), pulse oximetry, pressure liters per second of air infused from an artificial respirator, arterial pressure, and expired carbon dioxide.

23. A computer program product comprising a non-transitory storage medium having program instructions embodied in the non-transitory storage medium, the program instructions when executed cause the computer system to perform the method of claim 1.

* * * * *